United States Patent [19]
Alexander

[11] Patent Number: 5,847,825
[45] Date of Patent: Dec. 8, 1998

[54] APPARATUS AND METHOD FOR DETECTION AND CONCENTRATION MEASUREMENT OF TRACE METALS USING LASER INDUCED BREAKDOWN SPECTROSCOPY

[75] Inventor: Dennis R. Alexander, Lincoln, Nebr.

[73] Assignee: Board of Regents University of Nebraska Lincoln, Lincoln, Nebr.

[21] Appl. No.: 947,449

[22] Filed: Sep. 25, 1997

Related U.S. Application Data

[60] Provisional application No. 60/026,704 Sep. 25, 1996.
[51] Int. Cl.[6] ................................................ G01N 21/63
[52] U.S. Cl. ............................................................. 356/318
[58] Field of Search ..................................... 356/317, 318

[56] References Cited

U.S. PATENT DOCUMENTS

| 5,042,947 | 8/1991 | Potzsche et al. |
| 5,075,794 | 12/1991 | DeAndrea |
| 5,128,882 | 7/1992 | Cooper et al. |
| 5,133,901 | 7/1992 | Peterson et al. |
| 5,135,550 | 8/1992 | Telchuk et al. |
| 5,379,103 | 1/1995 | Zigler ..................................... 356/318 |

OTHER PUBLICATIONS

Alexander et al., "Detection Limits of Heavy Metals in Soils by Laser–Induced Breakdown Spectroscopy", *OSA TOPS on Environmental Monitoring and Instrumentation* v. 8 pp. 8–13, 1996.

Hahn, et al., "Discrete Particle Detection and Metal Emissions Monitoring Using Laser–Induced Breakdown Spectroscopy", *Applied Spectroscopy* v.51 n.12 pp. 1836–1844, 1997.

Rusak et al., "Investigation of the Effect of Target Water Content on a Laser–Induced Plasma", *Applied Spectroscopy* v.51 n.12 pp. 1628–1631, 1997.

(List continued on next page.)

Primary Examiner—F. L. Evans
Attorney, Agent, or Firm—Suiter & Associates PC

[57] ABSTRACT

A method and apparatus for in situ detection and concentration measurement of trace elements in an analysis sample is disclosed. The invention uses laser induced breakdown spectroscopy (LIBS) wherein femtosecond pulsed laser energy is employed to produce the plasma. The femtosecond pulsed laser energy is focused on the analysis sample to produce the plasma and the resulting emission is delivered for spectral analysis. Because the method and apparatus of the present invention allow breakdown of the analysis sample without propagation of energy to the sample-air interface, a plasma is produced that consists essentially of sample materials without being contaminated by air plasma formation. Thus, the background emission is reduced and there is no need to wait for the plasma to cool down over time before detecting the spectral lines of the sample. Because there is no need to wait for cooling before spectral measurement, lower detection limits are possible. Furthermore, concentration measurement accuracy is improved using intensity rationing techniques since a calibration curve produced using the method and apparatus of the present invention is substantially more linear than those using the conventional nanosecond pulsed LIBS.

30 Claims, 3 Drawing Sheets

OTHER PUBLICATIONS

C. Sanford et al., "Portable, Battery–Powered, Tungsten Coil Atomic Absorption Spectrometer for Lead Determinations", *Applied Spectroscopy*, v.50, n.2, pp. 174–181, 1996.

K. Yamamoto et al., "Detection of Metals in the Environment Using a Portable Laser–Induced Breakdown Spectroscopy Instrument", *Applied Spectroscopy*, v.50, n.2, pp. 222–223, 1996.

R. Gobel et al., "Enhancing the Sensitivity of Chemical Sensors for Chlorinated Hydrocarbons in Water by the Use of Tapered Silver Halide Fibers and Tunable Diode Lasers", *Applied Spetroscopy*, v.49, n.8, pp. 1174–1177, 1995.

H. Kurniawan et al., "Laser–Induced Shock Wave Plasma in Glass and Its Application to Elemental Analysis", *Applied Spectroscopy*, v.9, n.8, pp. 1067–1072, 1995.

C. Brown et al., "UV–Visible Spectral Library Search with Mixtures", *Applied Spectroscopy*, v.49, n.7, pp. 1022–1027, 1995.

D. Cremers et al., "Remote Elemental Analysis by Laser-–Induced Breakdown Spectroscopy Using a Fiber–Optic Cable", *Applied Spectroscopy*, v.49, n.6, pp. 857–860, 1995.

D. Poulain et al., "Influences on Concentration Measurements of Liquid Aerosols by Laser–Induced Breakdown. Spectroscopy", *Applied Spectroscopy*, v.49, n.5, pp. 569–579, 1995.

X. Mao et al., "Temperature and Emission Spatial Profiles of Laser–Induced Plasmas During Ablation Using Time–Integrated Emission Spectroscopy", *Applied Spectroscopy*, v.49, n.7, pp. 1054–1062, 1995.

D. Anderson et al., "Depth Profile Studies Using Laser–Induced Plasma Emission Spectrometry", *Applied Spectroscopy*, v.49, n.6, pp. 691–701, 1995.

C. Lazzari, et al., "Detection of Mercury in Air by Time–Resolved Laser–Induced Breakdown Spectroscopy Technique", *Laser and Particle Beams*, v.12, n.3, pp. 525–530, 1994.

R. Wisbrun et al., "Detector for Trace Elemental Analysis of Solid Environmental Samples by Laser Plasma Spectroscopy", *Analytical Chemistry*, v.66, n.18, pp. 2964–2975, 1994.

M. Carrabba, et al., "Spectroelectrochemical Technologies and Instrumentation for Environmental and Process Monitoring", *Environmental and Process Monitoring Technologies*, v.1637, pp. 82–90, 1992.

U. Bochert, et al., "On–Line Aerosol anaysis by atomic Emission Spectroscopy", *Journal of Aerosol Science*, v.20, n.8, pp. 1525–1528, 1989.

D. Ottesen, et al., "Real–Time Laser Spark Spectroscopy of Particulates in Combustion Environments", *Applied Spectroscopy*, v.43, n.6, pp. 967–975, 1989.

D. Cremers, et al., "Detection of Chlorine and Fluorine in Air by laser–Induced Breakdown Spectrometry", *Analytical Chemistry*, v.55, pp. 1252–1256, 1983.

W. Flower et al., "A Laser–Based Technique to Continuously Monitor Metal Aerosol Emissions", *The Society of Photo–Optical Instrumentation Engineers*, v.1716, 1992.

R. Wisbrun et al., "Laser–Induced Breakdown Spectroscopy for Detection of Heavy Metals in Environmental Samples", *The Society of Photo–Optical Instrumentation Engineers*, v.1716, pp. 2–15, 1992.

M. Casini, et al., "Time–Resolved LIBS Experiment for Quantitative Determination of Pollutant Concentrations in Air", *Laser and Particle Beams*, v.9, n.2, pp. 633–639, 1991.

L., Radziemski et al., "Time–Resolved Laser–Induced Breakdown Spectrometry of Aerosols", *Analytical Chemistry*, v.55, 1246–1252, 1983.

APPARATUS AND METHOD FOR DETECTION AND CONCENTRATION MEASUREMENT OF TRACE METALS USING LASER INDUCED BREAKDOWN SPECTROSCOPY

RELATED APPLICATIONS

This application claims priority under 35 U.S.C. §119(e) based on Provisional application Ser. No. 60/026,704, filed Sep. 25, 1996.

BACKGROUND OF THE INVENTION

1. Field of the Invention

The present invention relates to a system and method for detecting trace elements in an analysis sample and, more particularly, for the detection and concentration measurement of elements in an analysis sample using laser induced breakdown spectroscopy (LIBS). The present invention employs a short pulsed femtosecond ($10^{-15}$ second) laser and allows for rapid element concentration measurements in harsh or remote locations and is particularly suited to the detection and measurement of heavy metal soil contamination, and is particularly addressed to the problem of continuum emissions as a limitation on lower concentration detection limits.

2. Description of the Prior Art

By the year 2020, more than 3000 national Superfund sites will be listed, with cleanup costs of over $150 billion. Department of Energy and Department of Defense estimates total over $2 trillion. Instrumentation in the analytical laboratory can provide accurate elemental analysis through techniques such as atomic absorption spectroscopy, emission spectroscopy techniques such as inductively coupled plasma emission spectroscopy, activation analysis, x-ray fluorimetry, and the like. However, it is estimated that laboratory analyses account for 80% of site characterization and up to 50% of total remediation costs. Thus, the cost of environmental remediation could be drastically reduced if site characterization could be performed in situ without the need for the elaborate sample collection and preparation procedures required for laboratory analysis, and without the need for shipping samples off-site for analysis in the laboratory.

The LIBS technique uses a pulsed laser to rapidly heat a sample causing vaporization, dissociation into atomic species, and ionization which produces a plasma or laser spark. As the plasma cools, the excited species relax and emit optical energy at characteristic wavelengths. The emission can be spectrally resolved to identify the elemental species that are present in the sample based on the presence of characteristic spectral lines. The concentration of the elemental species present is proportional to the intensity of the spectral lines produced.

It is known that LIBS using long pulsed, such as 5–10 nanosecond pulsed Nd:YAG lasers at a wavelength of 1.064 $\mu$m or 17–22 nanosecond pulsed Excimer lasers operating at a wavelength of 248 nm, may be used for remote sensing of heavy metals in contaminated environmental sites.

U.S. Pat. No. 5,379,103 to Zigler describes a mobile laboratory for the in situ detection of heavy metal contaminants using a nanosecond pulsed laser.

Yamamoto et al., *Applied Spectroscopy*, 50(2), 222–33 (1996) describe a portable LIBS instrument for analysis of metals in soil and lead in paint using a nanosecond pulsed laser which fits into a small suitcase.

Pulse energies from these long pulsed lasers vary, but are typically around 100 mJ. As such, the focused electric fields are strong enough to produce breakdown at the soil-air interface. When the laser pulse is on the order of 10 nanoseconds, a significant amount of the later part of the energy pulse goes into heating the plasma formed during the earlier part of the pulse through multiphoton ionization processes as well as through cascade ionization. The resulting plasma is formed from the soils as well as the surrounding air molecules. The plasma thus formed is very highly ionized which results in large amounts of continuum emission, especially at short time scales. The air molecules also contribute to the broad emission background observed in the LIBS spectrum when nanosecond laser pulses are used to produce the breakdown.

To avoid the difficulties of the broad emission background when using nanosecond pulsed lasers of the prior art, the broad continuum must be given time to decay before the desired spectra of the species for analysis are detected. This, however, has the disadvantage of limiting the use of the LIBS method when attempting to detecting ion species at low concentrations and is an additional source of error in the measurement. Zigler, U.S. Pat. No. 5,379,103, at columns 6–7, describes such a method of using of cool down time to reduce background emission and thus, improve the signal to noise ratio. Yamamoto et al., supra, describe a nanosecond pulsed LIBS system employing a nongated detection system due to size constraints. However, detection limits are on the order of parts per million and the system is described as being useful for screening tool. Also, the authors suggest that a gateable detector would be useful in minimizing background continuum and minimizing spectral interferences between species.

Another disadvantage of LIBS processes wherein the long pulsed nanosecond laser pulses are employed is the phenomenon of temperature dependent bleaching of some of the spectral emission lines as a result of elevated plasma temperatures.

Because the femtosecond laser pulses of the present invention have lower energies than nanosecond pulses, less damage to surrounding materials and less ablation of material being analyzed by the laser spark occurs. Furthermore, less energy is transmitted to the air and surrounding materials.

It is, therefore, an object of the present invention to provide an improved LIBS process for the detection and measurement of elements in an analysis sample, particularly as a remote sensing method for detection and measurement of heavy metals in contaminated sites.

Another object of the invention is to provide a LIBS method that can be used to analyze solid, liquid, and gaseous material; wherein both conducting and dielectric samples can be used; and wherein no elaborate preparation is necessary.

Another object of the present invention is to provide a LIBS process wherein sampling regions on the order of approximately 10 $\mu$m are possible and wherein the sample mass required is so small that the method is essentially non-destructive.

Another object of the present invention is to provide a LIBS process wherein analysis can be performed in-situ in harsh or dangerous environments.

Another object of the present invention is to provide a LIBS process with parts-per-billion capabilities and wherein such quantitative concentration data can be obtained in real-time.

Another object of the present invention is to provide a LIBS process which can be adapted to penetrometer systems and other probing techniques using fiber optics.

Another object of the present invention is to provide a process wherein sample vaporization and excitation are possible in a single step.

Another object of the present invention is to provide a process that eliminates most or substantially all of the interfering background continuum emission.

Another object of the present invention is to provide a process with a lower plasma temperature and reduced temperature dependent bleaching of spectral emission lines.

Yet another object of the present invention is to provide a process wherein the calibration curve produced by ratioing the spectral emission lines is significantly more linear, thus providing for increased accuracy in calibration of a LIBS instrument and in obtaining quantitative data.

Still further objects and advantages will become apparent from a consideration of the ensuing description and drawings.

SUMMARY OF THE INVENTION

The objects of the present invention are provided by a LIBS method for detecting elements in an analysis sample using a femtosecond laser to produce the breakdown.

The present invention can be considered an improvement over the art known LIBS processes using long pulsed (nanosecond) lasers, the improvement comprising the use of a femtosecond laser to produce the plasma.

It has been found that, in accordance with the present invention, that if a femtosecond pulsed laser is used to produce the plasma, a plasma is formed that consists essentially of the analysis sample with very little energy transferred to the surrounding materials. Thus, in analyzing a soil sample using the femtosecond pulse in accordance with the present invention, the plasma produced will consist essentially of soil materials with little contamination by air plasma formation. Accordingly, the background emission is reduced and there is a reduced need to time gate the detection of the plasma emission in order to give the plasma time to cool down before detecting the spectral lines of the ions in the sample, thus permitting a lower concentration detection limit.

By using a short femtosecond pulse, a new unique LIBS plasma arises containing essentially only materials in the soil, since virtually all of the energy is absorbed by the soil with only small amounts propagated to the surrounding air. Thus, the laser pulse only produces a small amount of ionization of the surrounding air molecules and thereby reduces the signal to noise ratio by eliminating most of the interfering continuum emission. While not bound by any particular theory, it is believed that as a result of the extremely short duration of ultra fast femtosecond laser pulses of the present invention, quasi steady state assumptions are no longer applicable since energy is coupled into a system on a time scale shorter than most electron-phonon or phonon-phonon processes.

The accuracy of LIBS is dependent on the calibration curve produced by ratioing the various emission lines. The present invention provides a calibration curve significantly more linear and increases accuracy for calibration and for obtaining quantitative data, particularly at the lower concentrations.

DETAILED DESCRIPTION OF THE INVENTION

Figure 1:
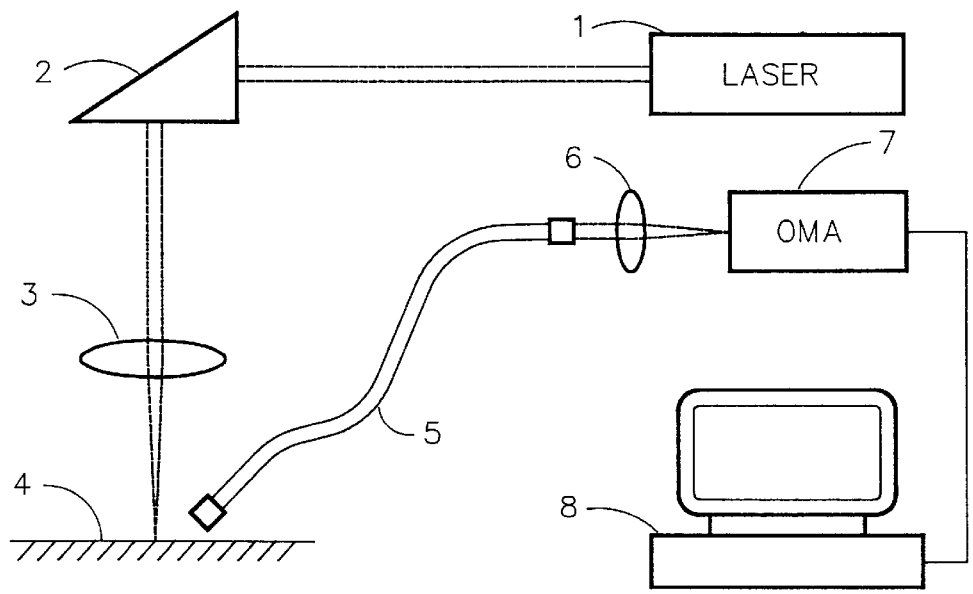
FIG. 1 shows a schematic diagram of the LIBS apparatus of the present invention.

The apparatus for the detection and concentration measurement of elements includes a femtosecond pulsed laser energy emitter and a means for delivering and focusing the laser energy emissions onto the analysis sample.

Lasers capable of generating pulses on the order of femtoseconds are known in the art and are commercially available. Common examples include dye lasers with compressed pulse means. In a typical embodiment of the LIBS process of the present invention, the femtosecond pulse laser energy emitter is an amplified Ti:sapphire femtosecond laser or a colliding pulse mode (CPM) laser. In a particularly preferred embodiment, an actively stabilized argon laser (Coherent Innova 306 Argon Laser) is used to pump the femtosecond laser to produce a very stable femtosecond pulse. See also, Murname et al., "The Recent Revolution in Femtosecond Lasers," *IEEE LEOS Newsletter*, August 1993, p. 17; Glanz, "Short-Pulse Lasers Deliver Terawafts on a Tabletop," *R&D Magazine*, April 1993, p. 54; and especially, Messenger, "Technology of Ultrafast Lasers and Electro-Optics Expands Rapidly," *Laser Focus World*, September 1993, p. 69. An overview of ultrafast laser sources is also described in commonly owned copending U.S. patent application Ser. No. 08/193,371, filed Feb. 7, 1994, which is hereby incorporated by reference in its entirety.

Any known means for delivering and focusing the pulsed laser energy emissions to the sample may be used. Such means include methods of delivering or steering the laser energy to the analysis sample, such as prisms, mirrors, lenses, optical fibers, optical crystals, and the like, and arrangements and combinations thereof.

The femtosecond laser pulses of the present invention range from about 1 attosecond to about 1000 femtoseconds, preferably from about 1000 femtoseconds, preferably from about 5 attoseconds to about several hundred femtoseconds, and more preferably from about 5 to about 500 femtoseconds. Shorter pulse lengths lead to plasma formation with less energy per pulse. The pulses are emitted at a frequency of from about 1 Hz to about 82 MHz.

In an alternative embodiment of the invention, an alternative means of plasma production may be used. For example, a pulsed ac spark or a pulsed arc from a pulsed dc power supply such as a rail gun spark apparatus may be used. The use of pulsed spark has the advantage of being less costly and more portable than the laser. However, the background emission is higher than with the femtosecond laser produced plasma due to increased continuum plasma.

The LIBS apparatus of the present invention also includes a means for delivering light emitted from the analysis sample for spectral analysis by a means for measuring spectral characteristics of such emitted light. As will be understood by those of ordinary skill in the art, any known means of delivering optical energy may be used, such as lenses, prisms, mirrors, optical fibers, optical crystals, and the like, and arrangements and combinations thereof. In a preferred embodiment of the present invention, the emitted light may be collected via a plasma emission collection lens. In an alternative preferred embodiment of the present invention, when there is sufficient emission intensity, the emitted light may be collected and delivered for spectral analysis directly by placing the end of the fiber optic cable near the region of the laser spark without the need for the use of a collecting lens to focus the emitted light.

Spectral analysis or spectral characteristics, as used herein, refer to the determination of the intensity of light as a function of wavelength. Means for such include a spectrophotometer, filter colorimeter, or optical multichannel analyzer, and the like.

The spectral analysis data can be output to a display, such as a cathode ray tube, a liquid crystal display, or a plasma display, directly and in real time.

In a preferred embodiment of the present invention, it is desirable to amplify the spectrograph through the use of an image intensifier tube and a multichannel analyzer photodiode array. The spectral analysis data can be output to a processor with a display monitor and/or data storage means, such as electromagnetic media or optical disk, for archiving data, which can used for later viewing and analysis or for producing a hard copy via a printer or plotter. Also, the processor may have a database of spectral characteristics stored in memory and means for comparing the measured spectral characteristics of the sample.

The concentrations of the metals in the analysis samples are determined by measurement of spectral line intensity. In a preferred embodiment, the image intensified diode array or CCD produces counts which can be displayed, stored, and compared to data control samples, calibration curves derived from control samples, or default values. In an especially preferred embodiment of the present invention, the processor has means for storing control, calibration, or default data and means for comparing the data from the sample thereto, thus allowing for essentially real time display of the spectral line intensities as a function of wavelength in terms of absolute concentration.

The control data may be generated using quantitative laboratory analysis of contaminated samples from the area of interest or by employing the LIBS method of the present invention using samples of known concentration of the substance or substances to be measured. In preparing control samples of known concentration, it is preferred to employ a matrix similar to that of the sample being analyzed. The controls may be prepared using the same element or elements to be detected or with another element or elements with similar rates of volatilization, similar excitation energies, lines in the same spectral region, and similar ionization potentials.

Although the present invention may be used for the measurement of any element desired, the present invention is particularly suited to the detection and measurement of metal, e.g., heavy metal, soil contamination. Examples of metal soil contaminants which may be detected and measured by the apparatus and method of the present invention include arsenic, bismuth, cadmium, chromium, mercury, lead, antimony, selenium, thallium, zinc, etc. but are not limited to these elements.

The present invention is also suited to determining soil quality, e.g., for agricultural applications. For example, trace quantities of boron, manganese, copper, molybdenum, and iron are required for plant growth. When the soil is deficient in one or more of the essential trace elements, crop yields may be reduced. Additionally, many such essential trace elements may be considered contaminants if present in concentrations that are too high. The method and apparatus of the present invention can be used to determine the concentration of these, and other elements, for the determination of soil quality and for formulating soil remediation plans as necessary.

When the sample to be analyzed is soil, the analysis can be performed at the surface or, can be performed at desired depths beneath the soil's surface through the use of a soil penetrometer system. Soil penetrometer systems are conventional in the art and are described in, for example, U.S. Pat. No. 5,128,882, which is hereby incorporated by reference in its entirety. The use of a soil penetrometer allows for the production of a continuous record of contaminant distribution in the soil on site and in real time.

The present LIBS method and apparatus may also be used in the detection of metals in mining operations and monitoring of waste products during the processing of minerals.

The method and apparatus of the present invention can also be used for the detection of lead in lead based paint, particularly in older homes and buildings.

The present invention is also useful monitoring process water or waste water in industrial processes. Examples include chlorine in the waste water of electronic chip manufacturing facilities or silicon buildup in the process water at chip manufacturing facilities. Also, the present process can be adapted to detecting contaminants in air, such as vaporized mercury, see, e.g., Lazzari et al., *Laser and Particle Beams*, 12(3), 525–30 (1994), or metal aerosol emissions from industrial processes, see, e.g., Flower et al., *Fuel Processing Technology*, 39, 277–84 (1994).

Additionally, the present invention is useful in monitoring heavy metals in fish and in the waterways of the world and for the detection of lead or other heavy metals of interest in a biological material such as cattle blood.

Referring now to the drawings and particularly to the embodiment of the present invention shown in FIG. 1, the LIBS system of the present invention is seen to comprise laser 1 capable of producing ultrafast femtosecond pulses, optical transmission media for directing the laser pulse and focusing lens 3 for focusing the femtosecond pulsed laser energy onto analysis sample 4, causing optical breakdown of the sample. Optical transmission media 2 may be any known means for delivering and focusing the pulsed laser energy emissions to the sample, including, for example, prisms, mirrors, optical media including optical fibers and optical crystals, and the like, and combinations thereof. The emissions from the plasma thus produced are collected and delivered for spectral analysis via fiber optic cable 5. Note that in this embodiment as depicted, the end of the fiber optic cable is sufficiently close to the analysis sample, and sufficient light can be collected without the need to focus the plasma emission onto the fiber. The collected light is transmitted via lens 6 to optical multichannel analyzer (OMA) 7 which is interfaced with computer 8 for real-time display of concentration information and for data storage and/or printing.

Figure 2:
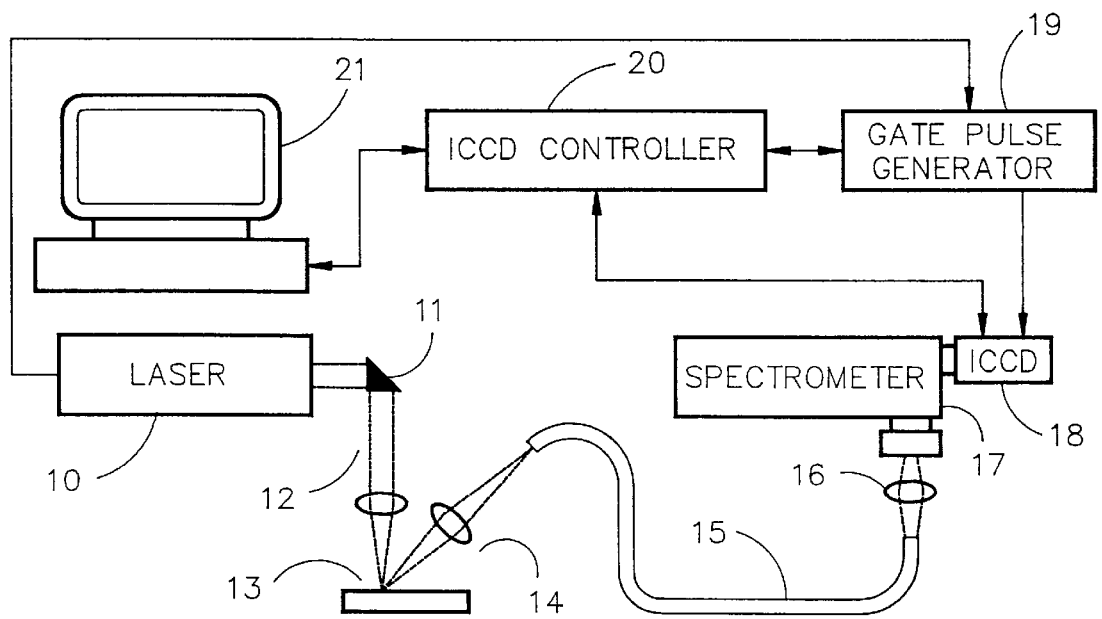
FIG. 2 shows a schematic diagram of the LIBS apparatus of a preferred embodiment of the present invention.

Referring now to FIG. 2, an alternative embodiment of the present invention is seen to comprise pulsed laser 10, prism 11, lenses 12, 14, and 16, used to focus the light onto analysis sample 13 and to couple the light emitted from the breakdown region to the location where the analysis is to be performed via fiber optic cable 15. Analysis is performed by spectrometer 17, intensified CCD camera 18, and ICCD controller 20, gate pulse generator 19, and computer 21 is for equipment control as well as data acquisition, display, and storage.

Figure 3A:
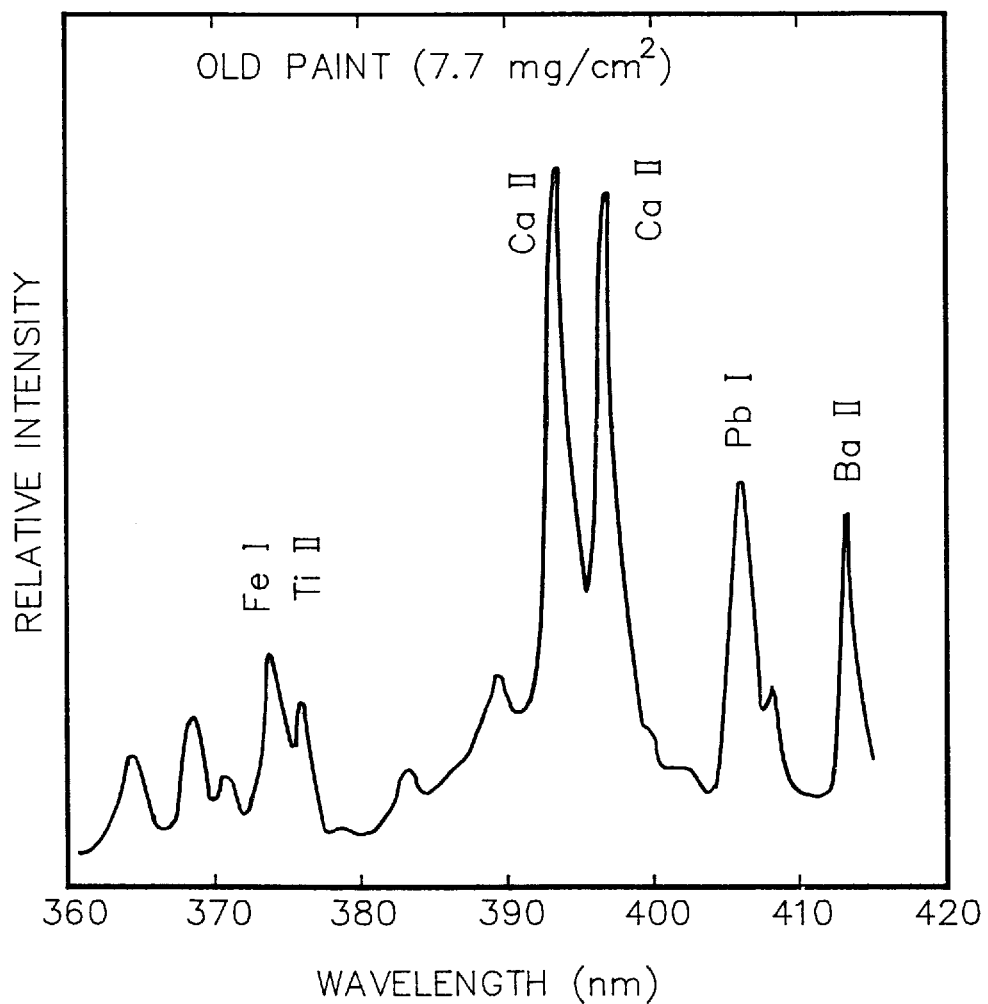
FIGS. 3A and 3B show plasma emission intensity as a function of wavelength for paint when the system and method of the present invention used to detect lead in/on walls painted with old paint and new paint, respectively.
Figure 3B:
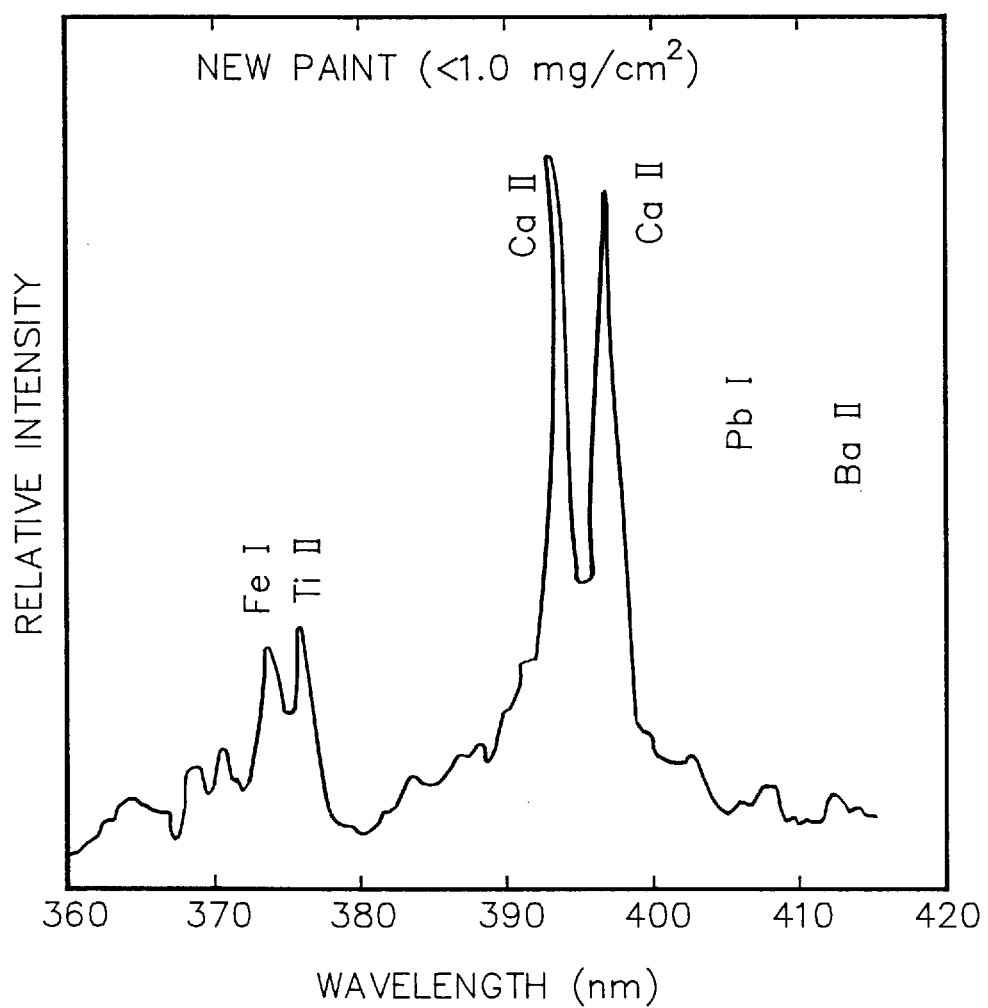

FIGS. 3A and 3B show plasma emission intensity as a function of wavelength for paint when the system and method of the present invention are used to detect lead in on walls painted with old paint and new paint, respectively. The concentration of lead in a sample of new paint is shown to be less than 1.0 mg/cm² and the concentration in a sample of old paint is 7.7 mg/cm².

The description above should not be construed as limiting the scope of the invention, but as merely providing illustrations to some of the presently preferred embodiments of this invention. In light of the above description and examples, various other modifications and variations will now become apparent to those skilled in the art without departing from the spirit and scope of the present invention as defined by the appended claims. Accordingly, the scope of the invention should be determined solely by the appended claims and their legal equivalents.

All references cited herein are hereby expressly incorporated by reference in their entireties.

What is claimed is:

1. An apparatus for measuring the contents of an analysis sample, comprising:
    (a) a pulsed laser energy emitter wherein the pulse length of said laser energy emitter is from about 1 attosecond to about 1000 femtoseconds in duration;
    (b) an optical transmission medium for focusing energy from said pulsed laser energy emitter onto said analysis sample, for generating a plasma state in a portion of said analysis sample; and
    (c) a detector for measuring spectral characteristics of energy emitted from said analysis sample when exposed to focused energy.

2. The apparatus of claim 1, wherein the pulse length of said laser energy emitter is from about 5 attoseconds to about 500 femtoseconds in duration.

3. The apparatus of claim 1, wherein said laser energy emitter emits pulses at a frequency of from about 1 Hz to about 82 MHz.

4. The apparatus of claim 1, wherein said optical transmission medium comprises one or more tenses.

5. The apparatus of claim 4, wherein said optical transmission medium further comprises transmission media for delivering pulsed laser energy to said one or more lenses.

6. The apparatus of claim 5, wherein said transmission media for delivering pulsed laser energy to said one or more lenses comprises optical fiber media.

7. The apparatus of claim 1, further comprising transmission media for delivering emitted energy from said analysis sample to said detector for measuring spectral characteristics of energy emitted from said analysis sample.

8. The apparatus of claim 7, wherein said transmission media for delivering emitted energy from said analysis sample to said detector for measuring spectral characteristics of energy emitted from said analysis sample comprises optical fiber media.

9. The apparatus of claim 1, wherein said detector for measuring spectral characteristics comprises a spectrograph and an optical multichannel analyzer.

10. The apparatus of claim 9, further comprising an image intensifier.

11. The apparatus of claim 1, further comprising a computer for storing spectral characteristics of predetermined substances and for comparing measured spectral characteristics to identify substances in said analysis sample.

12. The apparatus of claim 1, wherein trace elements are detected in said analysis sample by the presence of narrow spectral line characteristics.

13. The apparatus of claim 12, wherein the concentration of said trace elements in said analysis sample is determined by spectral line intensity or areas under spectral curves.

14. The apparatus of claim 13 wherein said trace elements comprise heavy metals.

15. The apparatus of claim 14 wherein said heavy metals are selected from the group consisting of chromium, lead, mercury, and zinc.

16. A method for measuring the content of an analysis sample comprising the steps of:
    (a) emitting laser pulses from a pulsed laser energy emitter wherein the pulse length of said laser energy emitter is from about 1 attosecond to about 1000 femtoseconds in duration;
    (b) focusing energy from said pulsed laser energy emitter on said analysis sample, thereby generating a plasma state in a portion of said analysis sample;
    (c) measuring spectral characteristics of energy emitted from said analysis sample when exposed to focused energy; and
    (d) detecting elements in said analysis sample by the presence of narrow spectral line characteristics.

17. The method of claim 16, wherein the pulse length of said laser energy emitter is from about 5 attoseconds to about 500 femtoseconds in duration.

18. The method of claim 16 further comprising the step of comparing measured spectral characteristics to entries in a database having predetermined spectral characteristics of known substances stored therein and identifying one or more substances present in said analysis sample based on the comparison.

19. The method of claim 18 wherein said comparison is performed by a processor.

20. The method of claim 16, wherein said laser pulses are emitted at a frequency of from about 1 Hz to about 82 MHz.

21. The method of claim 16, wherein energy from said pulsed laser energy emitter is focused onto said analysis sample using one or more lenses.

22. The method of claim 16, further comprising the step of transmitting said pulsed laser energy using optical fiber media.

23. The method of claim 16, further comprising the step of transmitting emitted energy from said analysis sample to a detector using optical fiber media said detector for measuring spectral characteristics of energy emitted from said analysis sample.

24. The method of claim 16, wherein said detector comprises a spectrograph and an optical multichannel analyzer.

25. The method of claim 24, wherein said detector further comprises an image intensifier.

26. The method of claim 16, further comprising the step of comparing measured spectral characteristics to stored spectral characteristics of predetermined substances to identify substances in said analysis sample.

27. The method of claim 16, wherein trace elements are detected in said analysis sample by the presence of narrow spectral line characteristics.

28. The method of claim 27, further comprising the step of determining the concentration of said trace elements in said analysis sample is determined by spectral line intensity or area tinder the spectrum.

29. The method of claim 16 wherein said trace elements comprise heavy metals.

30. The method of claim 29 wherein said heavy metals are selected from the group consisting of chromium, lead, mercury, and zinc.

* * * * *

UNITED STATES PATENT AND TRADEMARK OFFICE
CERTIFICATE OF CORRECTION

PATENT NO. : 5,847,825
APPLICATION NO. : 08/947449
DATED : December 8, 1998
INVENTOR(S) : Alexander Page 1 of 1

It is certified that error appears in the above-identified patent and that said Letters Patent is hereby corrected as shown below:

Col. 1 Line 6 and 7 change to:
Rights in the United States Government

This invention was made with federal support under the following research grant: N00014-90-C-3228 awarded by the United States Navy/ONR. The United States government has certain rights to this invention.

Signed and Sealed this

Twenty-fourth Day of February, 2009

JOHN DOLL
*Acting Director of the United States Patent and Trademark Office*